United States Patent [19]

Martin et al.

[11] Patent Number: 4,740,273

[45] Date of Patent: Apr. 26, 1988

[54] PROCESS FOR THE PURIFICATION OF DIETHOXYMETHANE FROM A MIXTURE WITH ETHANOL AND WATER

[75] Inventors: Daniel L. Martin; Peter W. Raynolds, both of Kingsport, Tenn.

[73] Assignee: Eastman Kodak Company, Rochester, N.Y.

[21] Appl. No.: 39,207

[22] Filed: Apr. 16, 1987

[51] Int. Cl.$^4$ .......................... B01D 3/36; C07C 43/30
[52] U.S. Cl. .......................... 203/39; 203/45; 203/46; 203/53; 203/55; 203/56; 203/63; 203/81; 203/83; 203/95; 568/594
[58] Field of Search ................ 203/39, 14, 19, 43–46, 203/53, 55, 56, 63, 62, 92, 93, 95–97; 568/594, 591, 918

[56] References Cited

U.S. PATENT DOCUMENTS

| | | | |
|---|---|---|---|
| 1,850,836 | 3/1932 | Guinot | 568/594 |
| 2,423,795 | 7/1947 | Patterson | 203/39 |
| 2,617,757 | 11/1952 | Michael | 203/53 |
| 2,827,495 | 3/1958 | Bond et al. | 568/594 |
| 3,024,170 | 3/1962 | Othmer et al. | 203/95 |
| 3,880,941 | 4/1975 | Davegardh et al. | 203/95 |
| 4,024,159 | 5/1977 | Peterson | 568/594 |
| 4,330,374 | 5/1982 | O'Keefe et al. | 203/39 |
| 4,491,676 | 1/1985 | Eagar et al. | 568/594 |
| 4,492,613 | 1/1985 | Wootton | 203/39 |
| 4,613,411 | 9/1986 | Hsu et al. | 203/67 |

OTHER PUBLICATIONS

J. N. Zaganiaris, Chem. Ber., 71, p. 2002 (1983), N. A. Pozdnyak, Sbornik Statei Obschchei Khim, 2, p. 1014 (1953).
(Chemical Abstracts vol. 49—6855e).

Primary Examiner—Wilbur Bascomb
Attorney, Agent, or Firm—Thomas R. Savitsky; William P. Heath, Jr.

[57] ABSTRACT

A process for purifying diethoxymethane from a mixture containing ethanol and, optionally, water. The process involves the addition of an amount of water, DEM, or an appropriate mixture of any two or three of water, DEM and ethanol that is effective in moving the mixture into the two liquid phase region on an equilibrium tie-line which crosses the critical distillation boundary without the need for additional azeotrope-forming agents such as cyclohexane.

26 Claims, 4 Drawing Sheets

PROCESS FOR THE PURIFICATION OF DIETHOXYMETHANE FROM A MIXTURE WITH ETHANOL AND WATER

DESCRIPTION

1. Technical Field

The present invention relates to a process for purifying diethoxymethane (DEM) from a mixture containing DEM, ethanol, and, optionally, water. This is accomplished by addition of an effective amount of water, DEM or an appropriate mixture of any two or three of water, DEM and ethanol, without the need for other azeotrope-forming agents.

2. Background of the Invention

Diethoxymethane is a valuable intermediate for the preparation of compounds used in the agricultural industry, the perfume industry and the paint industry. For example, diethoxymethane can be reacted with ketene to form ethyl-3-ethoxypropionate which is used as a paint solvent, particularly in paint for automobiles.

Certain known procedures for the preparation of diethoxymethane involve the acid-catalyzed equilibrium controlled reaction of formaldehyde with ethanol. See J. N. Zaganiaris, Chem. Ber., 71, p. 2002 (1983); and N. I. Shulkin and N. A. Pozdnyak, *Sbornik Statei Obschchei Khim.*, 2, p. 1014 (1953). Such procedures can be illustrated by the following exemplary reaction scheme:

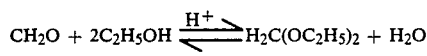

$$CH_2O + 2C_2H_5OH \underset{}{\overset{H^+}{\rightleftharpoons}} H_2C(OC_2H_5)_2 + H_2O$$

In preparing diethoxymethane commercially from the reaction of formaldehyde and ethanol, it is difficult to separate or purify the diethoxymethane from the azeotropes it forms with both ethanol and water. Methods known in the prior art for purifying diethoxymethane from such an azeotropic mixture involve the addition of an additional azeotrope-forming agent to the azeotropic mixture (e.g., see U.S. Pat. Nos. 1,850,836 and 4,613,411). This is disadvantageous in that such additional azeotrope-forming agents add to processing costs and are solvents such as hexane or cyclohexane which can be expensive, toxic, and potentially dangerous due to low flash points.

It would be desirable to have a process for purifying diethoxymethane which doesn't require the additional azeotrope-forming agent.

SUMMARY OF THE INVENTION

It has now been discovered that diethoxymethane can be purified from a mixture containing DEM, ethanol, and, optionally, water by the addition of either water, DEM or an appropriate mixture of any two or three of water, DEM and ethanol and therefore not requiring an additional azeotrope-forming agent. More specifically, the present invention is directed to a process for purifying DEM from a first mixture comprising DEM, ethanol, and, optionally, water; said process comprising the steps of (a) adding to said first mixture an amount of either water, DEM, or an appropriate mixture of any two or three of water, DEM and ethanol effective to allow the first mixture to lie in the two liquid phase region of the ternary system of water, ethanol and DEM, such that the equilibrium tie-line crosses the critical distillation boundary which results in a second mixture of two liquid phases, and, the optional step of (b) separating the phases of the second mixture to obtain a product containing a higher proportion of diethoxymethane than that proportion present in the first mixture, and the optional step of (c) distilling the DEM-rich product obtained from step (b) to obtain substantially pure diethoxymethane.

As used herein the term "additional azeotrope-forming agent" refers to any agent or compound other than water, DEM, ethanol, or mixtures thereof; the term "formaldehyde" refers to formaldehyde in the form of formalin, paraformaldehyde, or trioxane; the term "critical distillation boundary" refers to the distillation boundary between the water/ethanol/DEM azeotrope and the DEM/water azeotrope, such boundary is illustrated in FIG. 1 which separates Region I from Region III; the term "DEM" refers to diethoxymethane.

DETAILED DESCRIPTION OF THE INVENTION

Figure 1:
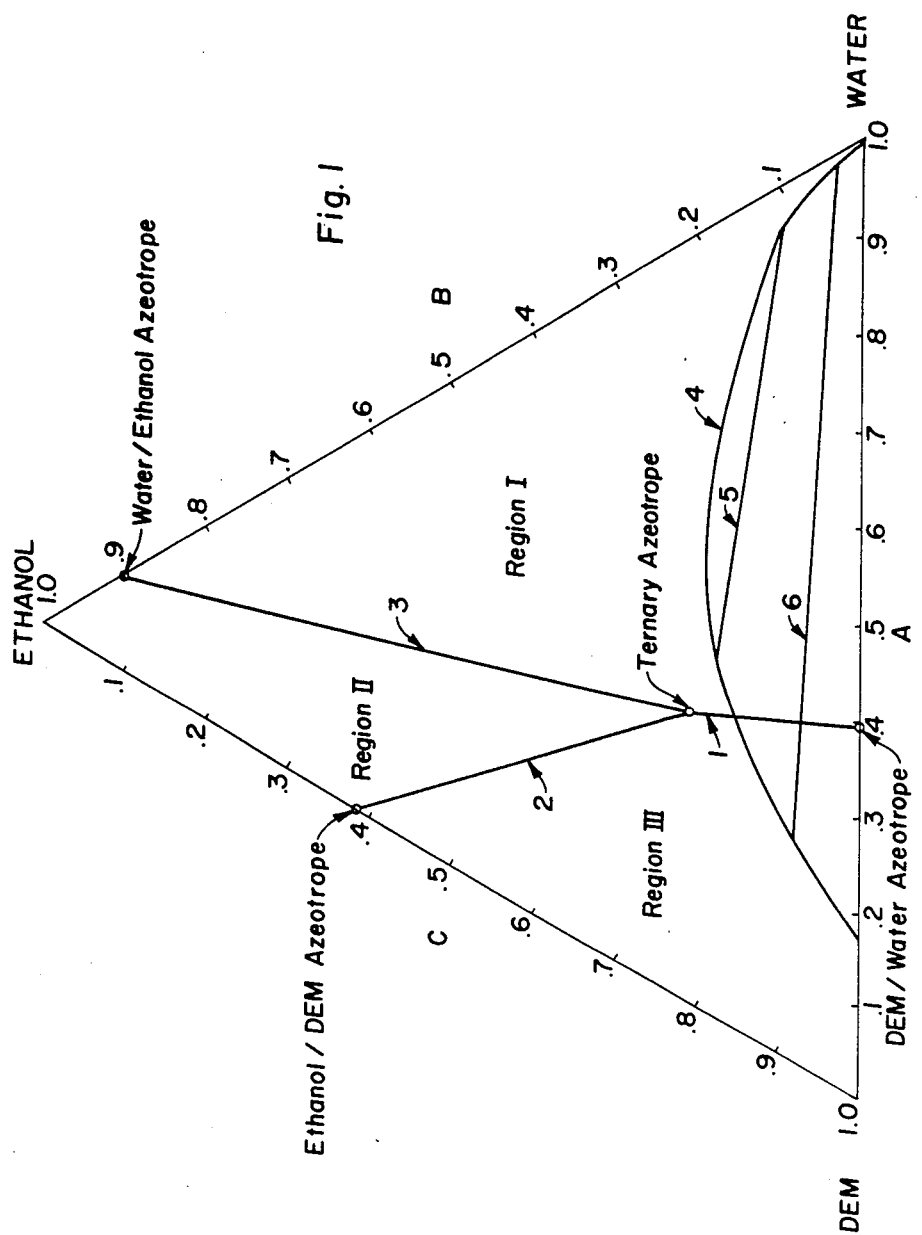
FIG. 1—Graph of the ternary azeotropic system of water, DEM, and ethanol. Scale A represents mole fraction of water, Scale B represents mole fraction of ethanol, and Scale C represents mole fraction of DEM. Line 1 approximates the critical distillation boundary. Line 2 approximates the distillation boundary between the ethanol/DEM azeotrope and the DEM/water/ethanol azeotrope. Line 3 approximates the distillation boundary between the ethanol/water azeotrope and the DEM/ethanol/water azeotrope. Line 4 approximates the boundary between the two liquid phase region and one liquid phase region. Lines 5 and 6 approximate exemplary tie lines; that is, lines that connect the compositions of two liquid phases which are in equilibrium with each other. As can be seen, tie-line 6 crosses the critical distillation boundary whereas tie-line 5 does not. (It should be noted that the location of the azeotropes in FIG. 1 is approximate.)

The present invention is based on our discovery that for the ternary system of DEM/ethanol/water the characteristic distillation boundaries can be crossed without an additional azeotrope-forming agent. Such boundaries are illustrated in FIG. 1. The ternary system, DEM/ethanol/water, has a minimum boiling homogeneous ternary azeotrope. In addition, there are homogeneous binary azeotropes of DEM/ethanol and ethanol/water and a heterogenous binary azeotrope of DEM/water. Between each of the azeotropes is a distillation boundary which cannot be crossed by simple distillation. These distillation boundaries divide the set of all ternary compositions into three regions. FIG. 1 is an approximation of the system with straight lines for the boundaries; however, it should be noted that the actual boundaries may not be straight (the location of the azeotropes is also approximate). Due to the distillation boundaries it is not possible to move from one region to another by simple distillation. However, for commercial processes, it is desired to recover DEM in pure form, remove water from the system, and recover the ethanol for recycle to the reactor(s) (the recycle ethanol can be in the form of the ethanol/water azeotrope, but does not have to be, e.g., it can be pure ethanol.) FIG. 1 shows that DEM and water are in two different Regions. As a result, no matter what the composition of the reaction mixture from the DEM reactor (i.e., the first mixture), it is necessary to at least cross the distillation boundary between the homogenous DEM/water/ethanol azeotrope and the heterogenous DEM/water azeotrope. Such distillation boundary is approximated in FIG. 1 as separating Region I from Region III; as mentioned hereinabove, this distillation boundary is referred to herein as the "critical distillation boundary". Due to the partial immiscibility of water and DEM, there is a heterogeneous liquid region for the ternary system where ethanol partitions itself between the DEM and the water phases. The two liquid phase region and the slope of the tie-lines are such that the distillation boundary between the homogenous DEM/water/ethanol azeotrope and the heterogenous DEM/water azeotrope can be crossed using liquid-liquid extraction (such as a single stage decanter, a multistage liquid-liquid extractor, and the like). Therefore, we have discovered that adding either water, DEM or an appropriate mixture of any two or three of water, DEM and ethanol to the first mixture in an effective quantity will result in an overall composition of the resulting mixture in the two liquid phase region and the two liquid phases formed are on opposite sides of the critical distillation boundary. Once step (a) of the process of the invention is performed (e.g., adding water); step (b) may then be carried out.

The exact substance (i.e., either water, DEM, or an appropriate mixture of any two or three of water, DEM, and ethanol) that is desired to be added to the first mixture will depend upon where said first mixture lies in the ternary system. Therefore, "an appropriate mixture" of any two or three of water, DEM, and ethanol refers to any proportion of compounds that, when added to the first mixture, will result in the mixture being in the desired two-liquid phase region on two sides of the critical distillation boundary. The exact proportion, as well as the exact composition of the substance, desired for a particular applicaition will depend upon where in the ternary system that the first mixture lies. As is clearly evident from FIG. 1, adding only ethanol will, in all situations, move the mixture further away from the two liquid phase region; therefore, adding only ethanol is not suitable for the process of the invention. For typical industrial processes, the first mixture will lie in Region I of FIG. 1 near the ternary azeotrope, and therefore it is most cost effective in such situations to simply add an effective amount of water.

Typically, the first mixture contains water, but it need not for the process of the invention to be useful. If no water is present in the first mixture, said mixture will be on the border of either Region II or Region III of FIG. 1 (i.e., 0.0 mole fraction of water). Therefore, if no water is present in the first mixture, water must be part or all of the substance added to said first mixture in order to achieve the desired results.

Addition of an effective amount of water, DEM, or an appropriate mixture of any two or three of water, DEM, and ethanol to the first mixture results in a two liquid phase mixture. The tie-line between the liquid phases crosses the critical distillation boundary (between Region I and Region III as illustrated in FIG. 1) which facilitates separation of DEM from the mixture. Such separation can be performed by decantation or other liquid-liquid extraction technique since a two liquid phase system is present, one phase of which is rich in DEM. The other phase, which contains mostly water and ethanol can be discarded; however, for commercial processes it is highly desired to separate the water from the ethanol, typically by use of another distillation column, in order to recycle the ethanol as part of the feed, i.e., starting material, for the DEM formation process. An alternative option is to return (recycle) the water-rich phase to the distillation column (or other unit, such as the reactor(s)) which produces the first mixture. The phase rich in DEM is preferably subjected to another step (Step (c)) to separate the DEM from the mixture in order to obtain substantially pure DEM. The separation of substantially pure DEM in step (c) is most conveniently accomplished by use of an additional distillation column where substantially pure DEM is removed as a product from the bottom of the distillation column.

It is preferred that the starting first mixture used in the process of the present invention is obtained by the reaction of formaldehyde, ethanol and an acid catalyst to form diethoxymethane and water and forcing the equilibrium of said reaction to the DEM and water side by removing one or more azeotropes containing diethoxymethane from the formaldehyde, ethanol, and acid catalyst reaction mixture. Such process is referred to herein as "the DEM formation process". Use of the DEM formation process in conjunction with the purification process of the present invention is most desirable in industrial applications wherein a continuous process is desired to form and purify commercial quantities of DEM. By use of a continuous process, various reactants and products can be recycled into the process system.

Although it is preferred to carry out the process of the present invention in a continuous manner, whether or not in conjunction with the DEM formation process, it is also comtemplated that said process can also be carried out batchwise.

The process of the present invention requires the addition of an effective amount of either water, DEM, or an appropriate mixture of any two or three of water, DEM and ethanol; however, other compounds or substances can also be present (in the first mixture or in the substance to be added) as long as the process of the invention is allowed to proceed. Such other compounds or substances can include methoxyethoxymethane (MEM) and other azeotrope-forming agents such as hexane or cyclohexane. However, as alluded to herein, it is preferred that the process of the present invention proceed in the absence of additional azeotrope-forming agents.

In the DEM formation process, substantially the same procedure taught in U.S. Pat. No. 4,613,411 can be employed. For example, formaldehyde is refluxed with ethanol in the presence of a soluble acid catalyst in one or more suitable reactors equipped with a distillation column. The distillate from such a distillation is suitable and is preferable for use as a starting material for the DEM purification process of this invention. Instead of using a distillate, the vapor phase from such a reaction can also be used as the first mixture.

The starting mixture for the DEM purification process, i.e., the first mixture, typically is obtained as a distillate from the DEM formation process. However, this is not required by the DEM purification process. A first mixture can contain, by weight, based on the total weight of the three components, from about 1 to about 99 percent DEM, from about 1 to about 99 percent by weight of ethanol, and from about 0 to about 99 percent by weight of water. A preferred first mixture can contain, by weight, based on the total of the three components, from about 15 to about 30 percent ethanol and at least 1 percent DEM.

As mentioned above, MEM is a typical impurity that is present in the starting mixtures of the present invention. The amount of MEM present in the first mixture for typical industrial process depends on the amount of methanol present in the formaldehyde feed for the DEM formation process. Formaldehyde containing less than about one percent methanol is commercially available and the amount of MEM present in the distillate of the DEM formation process is typically about two percent by weight of the total distillate.

Pressure for the process of the present invention (steps (a), (b) and (c)) is not particularly critical, although, for cost considerations, at or near atmospheric pressure is preferred. The temperature for Step (a) of the process must be between the freezing point of the mixture and the temperature at which the two liquid phase region no longer crosses the critical distillation boundary. For most applications, this temperature will be between 20° C. and 70° C. Temperature for Steps (b) and (c) of the process of the invention depends upon the pressure and the composition of the appropriate mixture, i.e., depends upon the saturated liquid temperature of the mixture. However, this temperature is between about 70° C. and about 150° C. for most applications (i.e., at or near atmospheric pressure).

The amount of either water, DEM, or an appropriate mixture of any two or three of water, DEM, and ethanol that must be added for step (a) will vary considerably depending on the exact composition of the starting mixture (i.e., first mixture) and the exact process parameters such as the temperature, pressure, size of reactors, columns, and the like. However, a typical amount of the substance to be added to a first mixture obtained from the DEM formation process is from about 0.2 to about one pound per pound of first mixture.

Suitable acids that are appropriate catalysts for the DEM formation process include strong acids such as sulfuric acid, p-toluenesulfonic acid, insoluble sulfonated polystyrenes, for example, Amberlyst 15, for instance, in a fixed bed. Preferred is sulfuric acid. The concentration of acid is not critical and can vary from about 0.01 to about 0.30 equivalents of acid per mole of formaldehyde. An excess of ethanol over formaldehyde is generally desirable, i.e., molar ratios of ethanol/formaldehyde in the range of from about 2 to 10:1 or higher are appropriate for the preferred DEM formation process.

Figure 2:
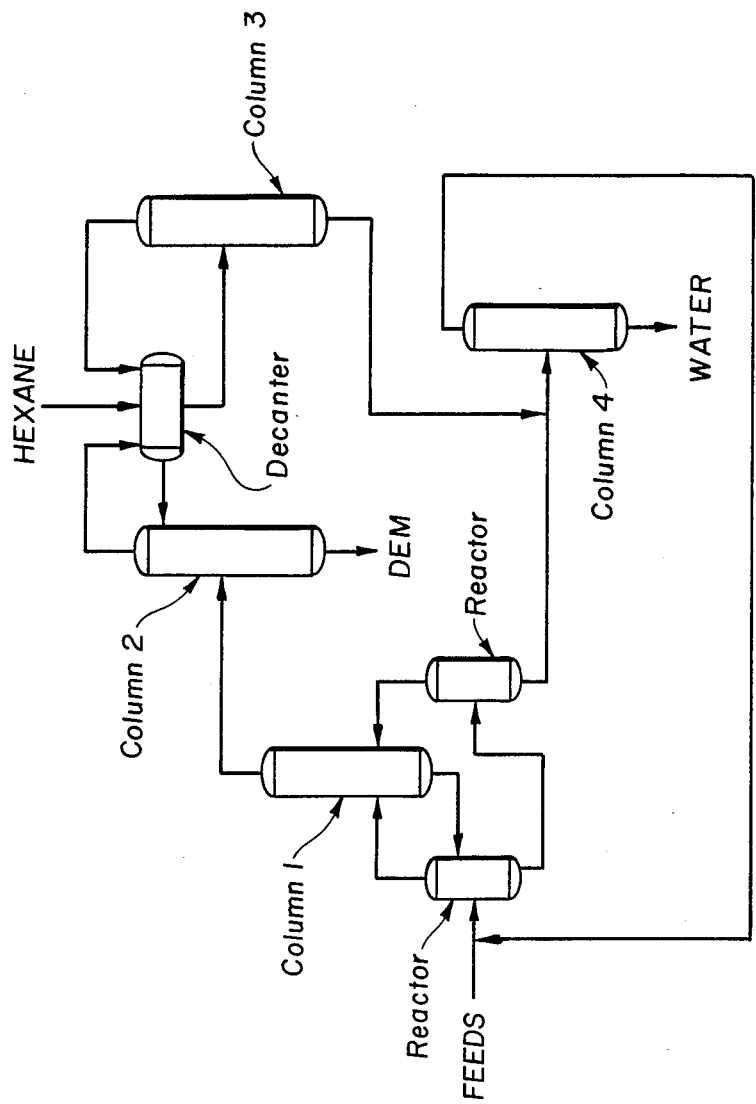
FIG. 2—A schematic representation of a typical prior art process for producing and purifying DEM employing four distillation columns.

As compared to prior art continuous processes for forming and purifying DEM, the process of the present invention is less complex and more economical. Depending on the specific embodiment, one or two distillation columns can be eliminated as compared to prior art processes. For example, FIG. 2 is a schematic representation of a typical process employing prior art technology, particularly that technology taught in U.S. Pat. No. 4,613,411. As can be seen, four distillation columns are required. The first distillation column (1) is to remove one or more azeotropes containing DEM from the reaction mixture which also contains formaldehyde, ethanol and acid catalyst. Distillation column 2 then is used to purify the DEM from the azeotropic mixture which has added an additional azeotrope-forming agent such as hexane. However, the additional azeotrope-forming agent must then be removed by a third distillation column (3) which leaves a water and ethanol mixture. The water and ethanol/water azeotrope must then be separated by a fourth distillation column (4). The four columns are necessary for such a process in order to have an economically feasible continuous process system.

Figure 3:
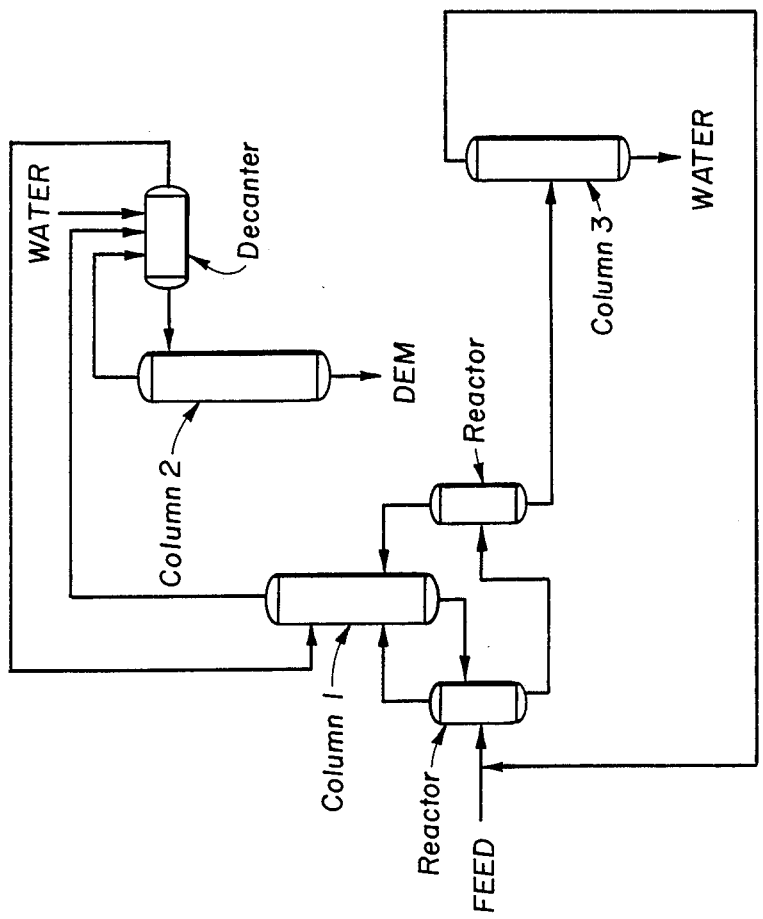
FIG. 3—A schematic representation of a preferred process of the present invention employing three distillation columns.

FIG. 3 illustrates a preferred embodiment of the present invention employing three distillation columns. In this embodiment two reactors are immediately upstream from a first distillation column (1). The DEM formation process occurs in the two reactors and the distillate from the first distillation column is the starting material for the DEM purification process. This distillate (the first mixture) is then fed to a decanter or other liquid-liquid extraction device where an effective amount of water, DEM, or an appropriate mixture of any two or three of water, DEM, and ethanol is added (step (a) of the DEM purification process). After the addition, which forms the second mixture, the two phases present are then separated by the decanter or other liquid-liquid extraction device (step (b) of the DEM purification process). The phase rich in DEM is then subjected to distillation in a second distillation column to obtain substantially pure DEM (step (c) of the DEM purification process). As can be seen in FIG. 3, a third column is employed to separate water from the water/ethanol azeotrope in order to recycle ethanol back into the reactors.

Figure 4:
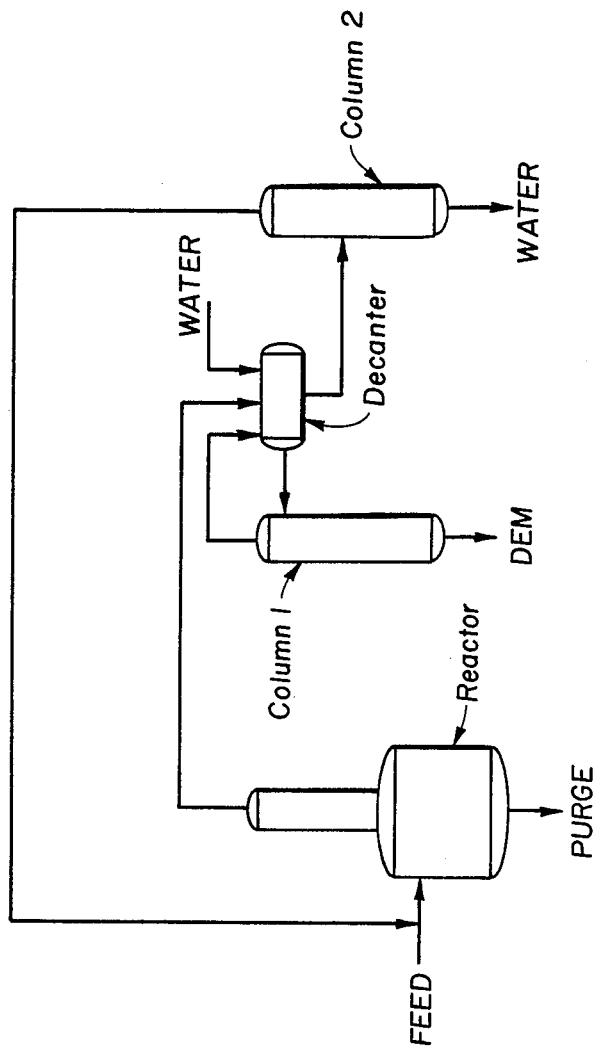
FIG. 4—A schematic representation of a preferred process of the present invention employing two distillation columns.

FIG. 4 illustrates another embodiment of the present invention wherein the first distillation column as discussed for FIG. 3 is eliminated. In this embodiment, the vapor phase from the reactor serves as the first mixture. After the DEM formation process occurs in the reactor, the vapor phase is condensed and fed to a decanter or other liquid-liquid extraction device where water, DEM or an appropriate mixture of any two or three of water, DEM and ethanol is added (step (a)) to form the second mixture. The two phases present are then separated by the decanter or other liquid-liquid extraction device (step (b)) and the phase rich in DEM is then subjected to distillation to obtain substantially pure DEM (step (c)). The phase not rich in DEM, i.e., containing primarily water and ethanol is subjected to distillation to remove water and obtain an ethanol/water azeotrope to recycle back as part of the feed in the reactor. The purge from the reactor is used to take small amounts of liquid from the reactor to avoid build-up of high molecular weight materials.

The following examples serve to illustrate the present invention, but should not be interpreted as a limitation thereon. All percentages are by weight unless indicated otherwise.

The following terms as used in the examples have the following definitions.

Aqueous phase or aqueous layer: The lower layer of the two phase system, containing a substantial amount of water along with ethanol and DEM.

Organic phase or organic layer: The upper, water immiscible mixture of DEM, ethanol, methoxyethoxymethane (MEM) and a small amount of water.

Crude DEM feed: That mixture of DEM, ethanol, water and MEM that is obtained from the reaction of ethanol and formaldehyde, after distillation ("first mixture").

EXAMPLE 1

This example illustrates separation of diethoxymethane from a mixture of diethoxymethane, water and ethanol, using a single equilibration by addition of water followed by distillation:

The apparatus consisted for a decanter and a distillation apparatus. The decanter was a 250 ml flask equipped with three inlets, an outlet for a lower water layer and an outlet for an upper organic layer. The distillation apparatus consisted of a 1 inch×24 inch packed column with a feed inlet at the sixteenth inch, a heated pot and a vapor dividing distillation head.

To the decanter was fed a mixture containing 8.9% water, 57.1% diethoxymethane (DEM) and 33.8% ethanol (EtOH). For each pound of the above mixture, 0.77 lb of water was added. In addition, the distillate from the distillation column was fed to the decanter. Two layers formed in the decanter. The lower, aqueous layer contained 70.2% water, 20.9% EtOH and 8.9% DEM. This lower layer was removed as required to keep the organic-water interface at the midpoint of the decanter. The recovery of EtOH DEM from this stream may be easily accomplished by simple distillation if desired. The upper, organic layer contained 4.3% water, 10.2% EtOH and 84.5% DEM. The organic layer was fed to the inlet of the distillation column, which was controlled to maintain a pot temperature of 89° C. and a head temperature of 72° C. The distillate, a mixture of DEM, EtOH and water, was returned to the decanter. The base of the distillation apparatus contained substantially pure DEM. For each pound of the above-described mixture of DEM, water and ethanol, 0.433 lb of DEM containing 0.07% EtOH and 0.03% water was recovered from the base.

EXAMPLE 2

This example illustrates removal of ethanol and water from a mixture of DEM, ethanol and water by continuous extraction with water.

The crude DEM feed for this run was made from ethanol and a commercial grade of formaldehyde containing about 1% of methyl alcohol. The methyl alcohol reacted as did ethanol, and a by-product, methoxyethoxymethane (MEM), was produced. It was observed that small amounts of MEM did not interfere with the separation as described below.

The apparatus consisted of a 1 inch×48 inch packed column. Provision was made to add water and remove organic material at the top, and to remove water and add organic material at the bottom. The water-organic interface was maintained about 1 inch above the bottom of the column. Water (80 grams/hour (g/h)) was fed to the top of the column, and 154 g/h of a mixture containing 8.3% water, 18.7% ethanol, 7.5% methoxyethoxymethane and 72.3% diethoxymethane was fed to the bottom of the column. The water percolated down the column and the aqueous phase exited at the bottom at a rate of 132.5 g/h. The aqueous phase contained 68.5% water, 21.1% ethanol, 0.2% MEM and 10.3% diethoxymethane. Ethanol, water and MEM can be conveniently separated from most of the water by distillation, if desired. The organic fraction exited the top of the column at a rate of 100 g/h. It contained mostly DEM along with small amounts of water, ethanol and MEM. Residual water, ethanol and MEM was removed by distillation as described in Example 1, and substantially pure DEM was obtained. This experiment used 0.5 pounds (lb) of water per pound of crude DEM mixture, causing 97.5% of the EtOH and 12.2% of the DEM to be extracted into the aqueous phase.

EXAMPLE 3

In an experiment similar to Example 2, using 1.3 lb of water per lb. of crude DEM mixture caused 99.8% of the ethanol and 17.0% of the DEM to be extracted into the aqueous phase. Thus, 185 g/h of water was added to the top of the column, and 147 g/h of a mixture containing 8.3% water, 22.1% ethanol, 0.3% MEM and 69.2% DEM was fed to the bottom. The organic phase containing 98.4% DEM, 0.07% ethanol, 0.38% MEM and 1.1% water was obtained at the top of the extractor.

This invention has been described in detail with particular reference to certain preferred embodiments thereof, but it will be understood that variations and modifications can be effected within the spirit and scope of the invention.

We claim:

1. A process for facilitating purifying diethoxymethane from a first mixture comprising an azeotropic system of diethoxymethane, ethanol, and optionally, water wherein said first mixture does not have an equilibrium tie-line that crosses a critical distillation boundary between a water/ethanol/diethoxymethane azeotrope and a diethoxymethane/water azeotrope, said equilibrium tie-line being a line that connects the compositions of two liquid phases which are in equilibrium with each other as represented in a graph of a ternary azeotropic system of water, diethoxymethane, and ethanol, said process comprising
(a) adding to said first mixture an amount of either water, diethoxymethane or an appropriate mixture of any two or three of water, diethoxymethane and ethanol effective to cause the first mixture to become a second mixture comprising a ternary azeotropic system of water, ethanol, and diethoxymethane, said second mixture being further characterized in that it comprises:
   (i) a first liquid phase that contains a higher proportion of diethoxymethane than that proportion of diethoxymethane present in said first mixture, and
   (ii) a second liquid phase that is not rich in diethoxymethane, said second mixture having an equilibrium tie-line that crosses said critical distillation boundary.

2. A process for purifying diethoxymethane from a first mixture comprising an azeotropic system of diethoxymethane, ethanol, and optionally, water wherein said first mixture does not have an equilibrium tie-line that crosses a critical distillation boundary between a water/ethanol/diethoxymethane azeotrope and a diethoxymethane/water azeotrope, said equilibrium tie-line being a line that connects the compositions of two liquid phases which are in equilibrium with each other as represented in a graph of a ternary azeotropic system of water, diethoxymethane, and ethanol, said process comprising
(a) adding to said first mixture an amount of either water, diethoxymethane or an appropriate mixture of any two or three of water, diethoxymethane and ethanol effective to cause the first mixture to become a second mixture comprising a ternary azeotropic system of water, ethanol, and diethoxymethane, said second mixture being further characterized in that it comprises:
  (i) a first liquid phase that contains a higher proportion of diethoxymethane than that proportion of diethoxymethane present in said first mixture, and
  (ii) a second liquid phase that is not rich in diethoxymethane,
said second mixture having an equilibrium tie-line that crosses said critical distillation boundary, and
  (b) separating the two liquid phases of the second mixture to obtain a product containing a higher proportion of diethoxymethane than that present in the first mixture.

3. A process for purifying diethoxymethane from a first mixture comprising an azeotropic system of diethoxymethane, ethanol, and optionally, water wherein said first mixture does not have an equilibrium tie-line that crosses a critical distillation boundary between a water/ethanol/diethoxymethane azeotrope and a diethoxymethane/water azeotrope, said equilibrium tie-line being a line that connects the compositions of two liquid phases which are in equilibrium with each other as represented in a graph of a ternary azeotropic system of water, diethoxymethane, and ethanol,
said process comprising
  (a) adding to said first mixture an amount of either water, diethoxymethane or an appropriate mixture of any two or three of water, diethoxymethane and ethanol effective to cause the first mixture to become a second mixture comprising a ternary azeotropic system of water, ethanol, and diethoxymethane, said second mixture being further characterized in that it comprises:
    (i) a first liquid phase that contains a higher proportion of diethoxymethane than that proportion of diethoxymethane present in said first mixture, and
    (ii) a second liquid phase that is not rich in diethoxymethane,
  said second mixture having an equilibrium tie-line that crosses said critical distillation boundary,
  (b) separating the two liquid phases of the second mixture to obtain a product containing a higher proportion of diethoxymethane than that present in the first mixture, and
  (c) distilling the product obtained from step (b) to obtain substantially pure diethoxymethane.

4. The process of claim 1 wherein said first mixture is obtained by the reaction of formaldehyde, ethanol and an acid catalyst to form diethoxymethane and water and forcing the equilibrium of said reaction to the diethoxymethane and water side by removing via distillation one or more azeotropes containing diethoxymethane from the formaldehyde, ethanol, and acid catalyst reaction mixture.

5. The process of claim 2 wherein said first azeotropic mixture is obtained by the reaction of formaldehyde, ethanol and an acid catalyst to form diethoxymethane and water and forcing the equilibrium of said reaction to the diethoxymethane and water side by removing via distillation one or more azeotropes containing diethoxymethane from the formaldehyde, ethanol, and acid catalyst reaction mixture.

6. The process of claim 3 wherein said first azeotropic mixture is obtained by the reaction of formaldehyde, ethanol and an acid catalyst to form diethoxymethane and water and forcing the equilibrium of said reaction to the diethoxymethane and water side by removing via distillation one or more azeotropes containing diethoxymethane from the formaldehyde, ethanol, and acid catalyst reaction mixture.

7. The process of claim 1 run continuously.

8. The process of claim 2 run continuously.

9. The process of claim 3 run continuously.

10. The process of claim 8 including the additional step of distilling the second phase not rich in diethoxymethane of the second mixture to obtain an ethanol/water azeotrope.

11. The process of claim 10 including the additional step of recycling the distilled ethanol/water azeotrope as a starting material for the diethoxymethane formation process.

12. The process of claim 1 carried out in the absence of an additional azeotrope-forming agent.

13. The process of claim 2 carried out in the absence of an additional azeotrope-forming agent.

14. The process of claim 3 carried out in the absence of an additional azeotrope-forming agent.

15. The process of claim 4 including the additional step of recycling the second phase not rich in diethoxymethane of the second mixture to the process unit which produces the first mixture.

16. The process of claim 5 including the additional step of recycling the second phase not rich in diethoxymethane of the second mixture to the process unit which produces the first mixture.

17. The process of claim 6 including the additional step of recycling the second phase not rich in diethoxymethane of the second mixture to the process unit which produces the first mixture.

18. The process of claim 7 including the additional step of recycling the second phase not rich in diethoxymethane of the second mixture to the process unit which produces the first mixture.

19. The process of claim 8 including the additional step of recycling the second phase not rich in diethoxymethane of the second mixture to the process unit which produces the first mixture.

20. The process of claim 9 including the additional step of recycling the second phase not rich in diethoxymethane of the second mixture to the process unit which produces the first mixture.

21. The process of claim 1 wherein water is added to the first mixture.

22. The process of claim 2 wherein water is added to the first mixture.

23. The process of claim 3 wherein water is added to the first mixture.

24. The process of claim 1 wherein said first mixture comprises from about 15 to about 30 percent ethanol, at least 1 percent DEM, said percentages being by weight and based on the total weight of ethanol plus DEM plus water.

25. The process of claim 2 wherein said first mixture comprises from about 15 to about 30 percent ethanol, at least 1 percent DEM, said percentages being by weight and based on the total weight of ethanol plus DEM plus water.

26. The process of claim 3 wherein said first mixture comprises from about 15 to about 30 percent ethanol, at least 1 percent DEM, said percentages being by weight and based on the total weight of ethanol plus DEM plus water.

* * * * *